United States Patent [19]

Heymes et al.

[11] Patent Number: 5,159,070
[45] Date of Patent: Oct. 27, 1992

[54] PROCESS FOR THE PREPARATION OF DERIVATIVE OF 7-[(2-HYDROXYIMINO)-ACETAMIDO]-CEPHALOSPORANIC ACID

[75] Inventors: René Heymes, Vezoul; Jean Jolly, Fontenay sous Bois; Primo Rizzi, Villemomble, all of France

[73] Assignee: Roussel Uclaf, Paris, France

[21] Appl. No.: 595,301

[22] Filed: Oct. 10, 1990

Related U.S. Application Data

[63] Continuation of Ser. No. 769,564, Aug. 26, 1985, abandoned, which is a continuation of Ser. No. 433,682, Oct. 12, 1982, abandoned, which is a continuation-in-part of Ser. No. 172,007, Jul. 24, 1980, abandoned.

[30] Foreign Application Priority Data

Jul. 26, 1979 [FR] France .................. 79 19295

[51] Int. Cl.⁵ .................. C07D 501/20; A61K 31/545
[52] U.S. Cl. .................... 540/222; 540/225; 540/227; 540/230
[58] Field of Search .............. 540/228, 227, 221, 230

[56] References Cited

U.S. PATENT DOCUMENTS 4,287,193  9/1981  Heymes et al. .............. 540/227
4,507,293  3/1985  Takaya et al. .............. 540/222

Primary Examiner—Nicholas S. Rizzo
Attorney, Agent, or Firm—Bierman and Muserlian

[57] ABSTRACT

A novel process for the preparation of syn isomers of cephalosporanic acid derivatives of the formula

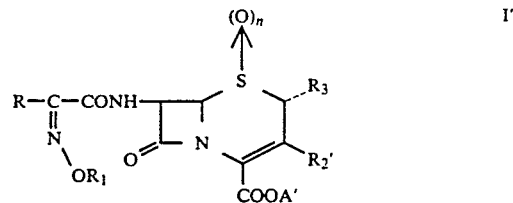

comprising reacting first in a solvent and optionally in the presence of a base, a compound of the formula

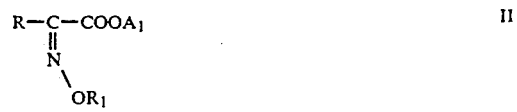

with a compound of the formula

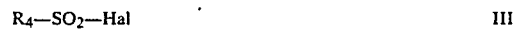

wherein $R_4$ is selected from the group consisting of optionally substituted alkyl, aryl and aralkyl and Hal is a halogen and reacting the resulting product in a solvent and optionally in the presence of a base with a compound of the formula

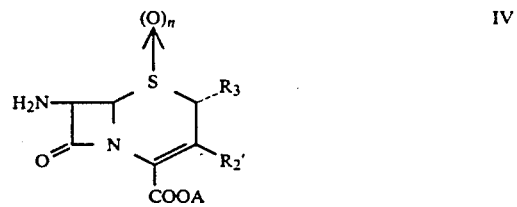

to obtain the compound of formula I' which are known to possess good antibiotic properties.

14 Claims, No Drawings

PROCESS FOR THE PREPARATION OF DERIVATIVE OF 7-[(2-HYDROXYIMINO)-ACETAMIDO]-CEPHALOSPORANIC ACID

PRIOR APPLICATION

This application is a continuation of U.S. patent application Ser. No. 769,564 filed Aug. 26, 1985 which in turn is a continuation of U.S. patent application Ser. No. 433,682 filed Oct. 12, 1982 which in turn is a continuation-in-part of our copending, commonly assigned U.S. patent application Ser. No. 172,007 filed Jul. 24, 1980, now all abandoned.

STATE OF THE ART

U.S. Pat. No. 4,287,193 describes the preparation of syn isomers by acylation of 7-amino-cephalosporanic acid with a symetric acid anhydride formed in the presence of dicyclohexylcarbodiimide, French patent No. 2,348,219 describes the acylation of 7-amino-cephalosporanic acid with reactive derivatives of 2-(2-amino-4-thiazolyl)-2-methoxyimino-acetic acid formed in the presence of dimethylformamide and phosphorus oxychloride. Also pertinent is Japanese patent application No. J 5-2051388.

OBJECTS OF THE INVENTION

It is an object of the invention to provide a process for the preparation of compounds of formula I directly in high yields.

This and other objects and advantages of the invention will become obvious form the following detailed description.

THE INVENTION

The novel process of the invention for the preparation of syn isomers of cephalosporanic acid derivatives of the formula

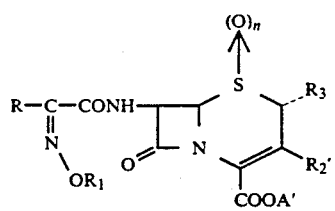

wherein R is selected from the group consisting of phenyl, thienyl, furyl and thiazoyl, optionally substituted with up to two groups selected from the group consisting of halogens, amino and protected amino, $R_1$ is selected from the group consisting of hydrogen, protective groups of the hydroxyalkyl of 1 to 6 carbon atoms, alkenyl and alkynyl of 2 to 6 carbon atoms and cycloalkyl of 3 to 6 carbon atoms, optionally substituted, and acyl of an organic carboxylic acid of 1 to 18 carbon atoms and when $R'_2$ is hydrogen, $R_3$ is selected from the group consisting of hydrogen and alkyl of 1 to 4 carbon atoms and when $R_3$ is hydrogen, $R'_2$ is selected from the group consisting of halogen, alkyl, alkoxy and alkylthio of 1 to 5 carbon atoms, cycloalkyl of 3 to 5 carbon atoms, acetoxymethyl carbamoyloxymethyl,

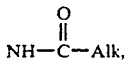

$-CH_2-S-R_5$, azidomethyl and

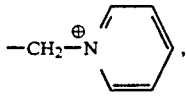

Alk is alkyl of 1 to 4 carbon atoms, $R_5$ is selected from the group consisting of 5 to 6 membered heterocycle containing 1 to 4 heteroatoms of S, N and O optionally substituted acyl of an alkanoic acid of 2 to 4 carbon atoms and condensed heterocycle, A' is selected from the group consisting of hydrogen, alkali metal, alkaline earth metal, magnesium, $-NH_4$, a non-toxic, pharmaceutically acceptable organic amine and ester or COOA' is $COO^-$, n is an integer from 0 to 2 with the proviso that when $R'_2$ is

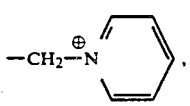

COOA' is $COO^-$, comprises reacting first in a solvent and optionally in the presence of a base, a compound of the formula

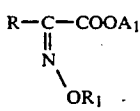

wherein R and $R_1$ have the above definition and $A_1$ is selected from the group consisting of hydrogen, alkali metal, alkaline earth metal, magnesium, $-NH_4$ and an organic amine base, with a compound of the formula

$R_4-SO_2-Hal$  III wherein $R_4$ is selected from the group consisting of optionally substituted alkyl, aryl and aralkyl and Hal is a halogen and reacting the resulting product in a solvent and optionally in the presence of a base with a compound of the formula

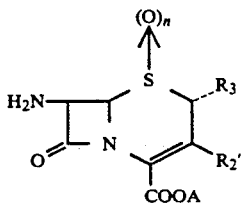

to obtain the compound of formula I'.

A particular mode of the process prepares syn isomers of compounds of the formula

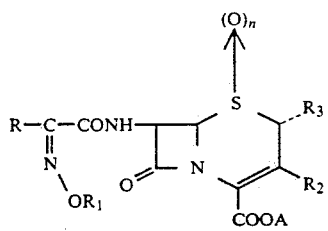

wherein R, $R_1$, $R_3$ and n have the above definition, $R_2$ has the definition of $R'_2$ except for

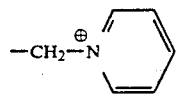

and COOA has the definition of COOA' except for —COO$^-$, starting from compounds of formula IV wherein $R'_2$ has the above values of $R_2$ and COOA' has the above value of COOA.

Preferred groups for R are 2-furyl, 1,3-thiazol-4-yl, 2-amino-5-chloro-1,3-thiazol-4-yl and especially 2-amino-1,3-thiazol-4-yl and protected 2-amino-1,3-thiazol-4-yl. When R is aryl, the aryl may be substituted with halogen such as fluorine, bromine, iodine and especially chlorine.

The protective group for the amino group may be alkyl of 1 to 6 carbon atoms, especially tert.-butyl or tert.-amyl; a aliphatic acyl or heterocyclic or aromatic acyl group or a carbamoyl group; a lower alkanoyl group such as formyl, acetyl, propionyl, butyryl, isobutyryl, valeryl, isovaleryl, oxalyl, succinyl or pivaloyl; alkoxycarbonyl or cycloalkoxycarbonyl such as methoxycarbonyl, ethoxycarbonyl, propoxycarbonyl, 1-cyclopropylethoxycarbony, isopropoxycarbonyl, butoxycarbonyl, tert.-butoxycarbonyl, pentyloxycarbonyl, tert.-pentyloxycarbonyl and hexyloxycarbonyl; benzoyl, toluolyl, naphthoyl, phthaloyl, mesyl, phenylacetyl, phenylpropionyl; and arylalkoxycarbonyl such as benzyloxycarbonyl.

The acyl group may also be substituted such as with a halogen like chlorine, bromine, iodine or fluorine. Such groups include chloroacetyl, dichloroacetyl, trichloroacetyl, trifluoroacetyl and bromoacetyl.

The amino protective group may also be aryloweralkyl such as benzyl, 4-methoxy-benzyl, phenethyl, trityl, benzhydryl or 3,4-dimethoxy-benzyl; haloalkyl such as trichloroethyl; chlorobenzoyl, p-nitrobenzoyl, p-tert.-butylbenzoyl, phenoxyacetyl, caprylyl, n-decanoyl, acryloyl, methylcarbamoyl, phenylcarbamoyl, naphthylcarbamoyl and the corresponding thiocarbamoyl. The said list is not intended to be exhaustive and may include other known protective groups such as those used in peptide chemistry.

The hydroxyl protective group of $R_1$ may be acyl such as formyl, acetyl, chloroacetyl, bromoacetyl, di-chloroacetyl, trichloroacetyl, trifluoroacetyl, methoxyacetyl, phenoxyacetyl, benzoyl, benzoylformyl or p-nitrobenzoyl; ethoxycarbonyl, methoxycarbonyl, propoxycarbonyl, benzyloxycarbonyl, tert.-butoxycarbonyl, 1-cyclopropylethoxycarbonyl, tetrahydropyranyl, tetrahydrothiopyranyl, methoxytetrahydropyranyl, trityl, benzyl, 4-methoxybenzyl, benzhydryl, trichloroethyl, 1-methyl-1-methoxyethyl or phthaloyl.

Equally useful as $R_1$ are other acyl groups such as propionyl, butyryl, isobutyryl, valenyl, isovaleryl, oxalyl, succinyl, and pivaloyl, phenylacetyl, phenylpropionyl, mesyl, chlorobenzyl, p-nitrobenzoyl. p-tert.-butyl-benzoyl, caprylyl, acryloyl, methylcarbamoyl, phenylcarbamoyl and naphthcarbamoyl as well as methyl, ethyl, propyl, isopropyl, butyl, sec.-butyl, tert.-butyl, pentyl, hexyl, vinyl, allyl, propargyl, ethynyl, cyclopropyl, cyclobutyl, cyclopentyl and cyclohexyl.

Examples of substituents of $R_1$ when optionally substituted ally, alkenyl, alkynyl and cycloalkyl with at least one member of the group consisting of tert.-butoxycarbonyl; carboxy, salified carboxy, nitrile, amino, alkylamino and dialkylamino; aryl, tetrazolyl, 4-methyl or 4-amino-thiazol-2-yl, pyridinyl; azido or arylthio, hydroxy, halogens, iodine and such as 2-bromo-propen-2-yl; acyl, group such as optionally substituted alkanoyl or carbamoyl; alkoxy and alkylthio; isoureido, thiocyanato, methylthio and aminohydrazino.

Among other values of $R_1$, the preferred groups are acyl as indicated above, aroyls groups such as optionally substituted benzoyl, optionally substituted carbamoyl, aminoalkanoyl or substituted aminoalkanoyl.

$R_3$ in the 2-position of the cephem ring has the α-configuration and may be methyl, ethyl, propyl, isopropyl, butyl, sec.-butyl or tert.-butyl.

Examples of $R_2$ and $R'_2$ are methyl, ethyl, propyl, isopropyl, butyl, sec.-butyl, tert.-butyl, pentyl, isopentyl, tert.-pentyl, neopentyl, cyclopropyl, cyclobutyl, cyclopentyl, methoxy, ethoxy, propoxy, butoxy isopropoxy, sec.-butyloxy, tert.-butyloxy, pentyloxy, isopentyloxy, tert.-pentyloxy, neopentyloxy, methylthio, ethylthio, propylthio, isopropylthio, butylthio, sec.-butylthio, tert.-butylthio, pentylthio, isopentylthio, tert.-pentylthio and neopentylthio as well as acetamido, propionylamido, butyrylamido and isobutyrylamido.

Examples of $R_5$ are acetyl, 1-methyl-tetrazolyl, 2-methyl-1,3,4-thiadiazolyl, 3-methyl-1,2,4-thiadiazol-5-yl, 3-methoxy-1,2,4-thiadiazolyl, 1,3,4-thiadiazol-5-yl; 2-amino-1,3,4-thiadiazol-5-yl, 3-hydroxycarbonylmethyl-1,2,4-thiadiazol-5-yl, 5-methoxy-1,2,4-thiadiazol-3-yl, 4-methyl-5-hydroxycarbonylmethyl-1,3-thiazol-2-yl, 1-dimethylaminoethyl-1,2,3,4-tetrazol-5-yl, 1,3,4-triazol-5-yl, 2-(thien-2-yl)-1H-1,3,4-triazol-5-yl, 1-amino-2-trifluoromethyl-1,3,4-triazol-5-yl, and 4-hydroxycarbonylmethyl-1,3-thiazol-2-yl.

Examples of A or A' are salts such as sodium, potassium, lithium, calcium, magnesium, diethylamine, trimethylamine, methylamine, propylamine, ethanolamine, N,N-dimethylethanolamine, and esters such as butyl, isobutyl, tert.-butyl, pentyl, hexyl, benzhydryl, p-methoxybenzyl, 3,4-dimethoxybenzyl, acetoxymethyl and pivaloyloxymethyl.

The reaction of the compounds of formulae II and III is preferably effected in an anhydrous organic solvent such as acetone, dimethylformamide, ethylacetate, tetrahydrofuran, acetonitrile, carbon tetrachloride, chloroform, methylene chloride, toluene, xylene, dioxane, ether, isopropyl ether, N-methyl-pyrrolidone or dimethylacetamide.

When the compound of formula II is used in the free acid form (A is hydrogen), the sulfonyl halide of formula III is preferably reacted in the presence of a base such as triethylamine, N,N-dimethylaniline, tributylamine, N-methylmorpholine, pyridine, picoline, sodium carbonate, sodium bicarbonate, potassium carbonate or potassium bicarbonate. The preferred base is triethylamine. When the compound of formula II is in the form of a salt, the reaction with the sulfonyl halide of formula III is preferably effected in the absence of a base.

The sulfonyl halide of formula III is preferably tosyl chloride although other sulfonyl chlorides such as methane sulfonyl chloride may be used.

The reaction of the compounds of formulae II and III may be effected at room temperature or with cooling. When R is a group containing an unprotected amino group, it is preferred to effect the reaction for the formation of a reactive derivative of formula II with cooling, particularly on the order of $-25°$ to $0°$ C.

The reactive derivative of the compound of formula II which is formed in the first step of the process appears to be a mixed carboxylic-sulfonic acid anhydride of the formula

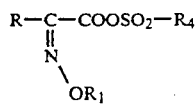

In two of the examples, the mixed anhydride has been isolated by crystallization and was characterized.

The second step of the process of the invention consists of acylating 7-amino-cephalosporanic acid or one of its derivatives of formula IV and the reaction is preferably effected by adding the solution of the first reaction step to a solution of a compound of formula IV.

When A or A' are not a salt, the compound of formula IV is dissolved by operating in the presence of a base, preferably triethylamine. Examples of suitable solvents are preferably aqueous dimethylacetamide and methylene chloride although other solvents may be used as the selection of the solvent is not critical for this step. The said reaction is preferably effected at a low temperature, most preferably between $-75°$ and $5°$ C.

Naturally, depending upon the substituents A or A' and R or $R_1$, the steps of the process may be followed, if necessary, by purification steps or cleavage of one or more protective groups which steps are known in the literature. The process may also be followed by salification or esterification to obtain the desired compounds.

As compared to the process of Belgium patent No. 850,662, the process of the invention has the advantage of requiring just one equivalent of a 2-aryl-2-oxyiminoacetic acid. The product of the present process are directing obtained in pure form and in excellent yields as compared to the process of French patent No. 2,348,219 which requires purification by chromatography with a silica gel column.

A preferred mode of the process of the invention for the preparation of the syn isomer of a compound of the formula

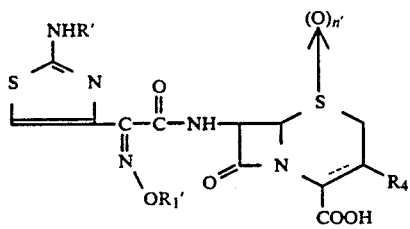

wherein R' is selected from the group consisting of hydrogen and an amino protective group, $R'_1$ is selected from the group consisting of hydroxy protective group, alkyl of 1 to 4 carbon atoms optionally substituted with a free or esterified carboxyl and alkenyl and alkylnyl of 2 to 4 carbon atoms, $R_4$ is selected from the group consisting of hydrogen and $—CH_2—R''_2$, $R''_2$ is selected from the group consisting of acetoxy, 1-methyl-1(H)-tetrazol-5-ylthio, 2-methyl-1,3,4-thiadiazolylthio and azido and n' is 0 or 1, comprises reacting in a solvent and in the optional presence of a base a compound of the formula

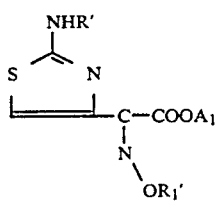

wherein R' and $R'_1$ have the above definition and $A_1$ is selected from the group consisting of hydrogen, alkali metal, alkaline earth metal, $—NH_4$, magnesium and an organic amine base with tosyl chloride and reacting the resulting product in a solvent and in the presence of a base with a compound of the formula

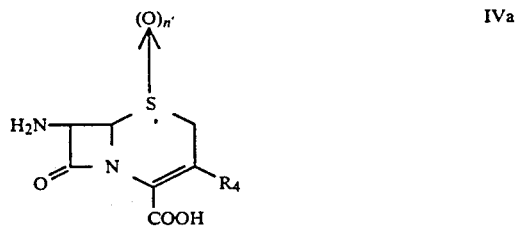

wherein n' and $R_4$ have the above definition.

In the latter process, $R'_1$ is preferably methyl or isopropyl optionally substituted with an alkoxycarbonyl of 2 to 6 carbon atoms, especially tert.-butoxycarbonyl.

In an especially preferred mode of the process of the invention, the solvent for the reaction of the compounds of formulae II and III or tosyl chloride and the compound of formula $II_A$ is selected from the group consisting of acetone, dimethylacetamide, ethyl acetate, tetrahydrofuran, acetonitrile, carbon tetrachloride, methylene chloride, toluene, dioxane, isopropyl ether, N-methyl-pyrrolidone and dimethylformamide and the most preferred solvent is dimethyl acetamide. The reaction with the compound of formula IV or $IV_A$ is preferably effected in methylene chloride or in aqueous dimethyl acetamide and the base optionally required in the different phases of the process is triethylamine and both steps are effected at low temperatures.

A preferred embodiment of the process of the invention comprises reacting at low temperatures in dimethylacetamide in the presence of triethylamine, tosyl chloride and the syn isomer of 2-(2-amino-4-thiazolyl)-2-methoxyimino-acetic acid and reacting the resulting product with 7-amino-cephalosporanic acid in methylene chloride in the presence of triethylamine to obtain the syn isomer of 3-acetoxymethyl-7-[2-(2-amino-4-thiazolyl)-2-methoxyimino-acetamido]-ceph-3-eme-4-carboxylic acid.

Another preferred embodiment of the process of the invention comprises reacting at low temperatures in dimethylacetamide in the presence of triethylamine, tosyl chloride and the syn isomer of 2-(2-tritylamino-4-thiazolyl)-2-methoxyiminoacetic acid and reacting the resulting product with a solution of 7-amino-cephalosporanic acid in methylene chloride in the presence of triethylamine to obtain the syn isomer of 3-acetoxymethyl-7-[2-(2-tritylamino-4-thiazolyl)-2-methoxyimino-acetamido]-ceph-3-eme-4-carboxylic acid.

The compound of formula II wherein R is aminothiazolyl or protected aminothiazolyl are described in Belgium Patent No. 850,662 and when R is phenyl, thienyl or furyl are described in French Patent No. 2,137,899. The compounds of formula II wherein R is thiazolyl may be prepared by starting with a compound of the formula

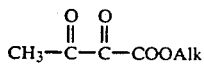

by the process of French patent No. 2,383,187 except that thiourea is replaced by thioformamide. The products obtained before saponification are reacted with a compound of the formula $NH_2—OR_1$ and are then saponified.

The compounds of formula II wherein R is thiazolyl substituted with amino and a halogen may be prepared by reacting a compound of formula II wherein R is aminothiazolyl with a halogenation agent.

The compounds of formula IV are known in the literature and, in particular, the compounds where n is 1 or 2 are described in French patent No. 2,387,234.

Besides the compounds produced in the following examples, the process is also useful for the preparation of the following compounds: The syn isomer of 3-[(1-methyltetrazol-5-yl)-thiomethyl]-7-[2-(2-amino-4-thiazolyl)-2-methoxyimino-acetamido]-ceph-3-eme-4-carboxylic acid, the syn isomer of 7-[2-(2-amino-4-thiazolyl)-2-methoxyimino-acetamido]-ceph-3-eme-4-carboxylic acid and the syn isomer of 3-carbamoyloxymethyl-7-[2-(fur-2-yl)-2-methoxyimino-acetamido]-ceph-3-eme-4-carboxylic acid and their easily cleavable esters and their alkali metal, alkaline earth metal, magnesium, —$NH_4$ and non-toxic, pharmaceutically acceptable organic amine salts.

Equally obtainable by the process of the invention after optional deblocking of the protective functions and salification are the syn isomer of 3-(1-pyridiniummethyl)-7-[2-(2-amino-4-thiazolyl)-2-(2-carboxyisopropoxyimino)-acetamido]-ceph-3-eme-4-carboxylic acid and the syn isomer of 3-acetoxymethyl-7-[2-(2-amino-4-thiazolyl)-2-(2-carboxyisopropoxyimino)-acetamido]-ceph-3-eme-4-carboxylic acid and their non-toxic, pharmaceutically acceptable salts and esters.

In the following examples there are described several preferred embodiments to illustrate the invention. However, it should be understood that the invention is not intended to be limited to the specific embodiments.

EXAMPLE 1

Syn isomer of 3-acetoxymethyl-7-[2-(2-tritylamino-4-thiazolyl)-2-methoxyimino-acetamido]-ceph-3-eme-4-carboxylic acid STEP A: p-toluene sulfonic 2-(2-tritylamino-4-thiazolyl)-2-methoxyimino-acetic acid anhydride A mixture of 44.3 g of 2-(2-tritylamino-4-thiazolyl)-2-methoxyimino-acetic acid, 15 ml of triethylamine and 250 ml of acetone was allowed to form a solution after which crystallization occured. The mixture was stirred in an ice bath for 10 minutes and was then vaccum filtered. The product was washed with acetone, then with ether and dried to obtain 46.4 g of the triethylamine salt of 2-(2-tritylamino-4-thiazolyl)-2-methoxyimino-acetic acid. A mixture of 59.92 g of the said triethylamine salt, 20.97 g of p-toluene sulfonyl chloride and 500 ml of acetone was stirred at room temperature for one hour and then for 15 minutes in an ice water bath. The mixture was vacuum filtered and the product was rinsed and dried to obtain 12.1 g of insoluble. The filtrate containing p-toluene sulfonic 2-(2-tritylamino-4-thiazolyl)-2-methoxyimino-acetic acid anhydride was held in an ice water bath until ready for use in Step B.

Analysis of dry extract fraction

NMR Spectrum (CDCl$_3$): peaks at 2.39 ppm

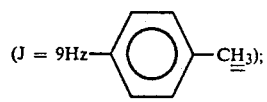

at 4.05 ppm (J=4 Hz=N—OCH$_3$); at 6.74 ppm (J=5.5 Hz 5-proton of thiazol); at 7.3 $\overline{ppm}$ (trityl).

I.R. Spectrum (CHCl$_3$): Absorption at 1821, 1782, 1760 and 1715 cm$^{-1}$ (C=O).

| U.V. Spectrum (ethanol): | |
|---|---|
| Inflex. towards 227 nm | $\epsilon = 26,200$ |
| Inflex. towards 237 nm | $\epsilon = 20,100$ |
| Inflex. towards 260 nm | $\epsilon = 12,600$ |
| Inflex. towards 267 nm | |
| Inflex. towards 272 nm | |
| Inflex. towards 295 nm | $\epsilon = 5,400$ |
| U.V. Spectrum (0.1N HCl-ethanol): | |
| Inflex. towards 227 nm | $\epsilon = 23,500$ |
| Inflex. towards 265 nm | |
| Max. at 275 nm | $\epsilon = 12,900$ |
| Inflex. towards 288 nm | |

STEP B: Syn isomer of 3-acetoxymethyl-7-[2-(2-tritylamino-4-thiazolyl)-2-methoxyimino-acetamido]-ceph-3-eme-4-carboxylic acid About 30 minutes after the preparation of the solution of Step A, a mixture of 27.2 g of 7-amino-cephalosporanic acid, 100 ml of water and 150 ml of a molar solution of sodium bicarbonate was stirred for 30 minutes at room temperature to obtain a complete dissolution (pH=7.2) and 150 ml of acetone were added thereto. The mixture was cooled to 5° C. in an ice-methanol bath and then the iced solution of Step A was added thereto over 15 minutes while maintaining the temperature at 5° C. Precipitation occured followed by dissolution and then 50 ml of a molar sodium bicarbonate solution were added thereto to adjust the pH to 7.85. The mixture stood for 90 minutes and then the acetone was distilled at 30° C. under reduced pressure. 100 ml of water and then 20 ml of 66% furmic acid were added to the mixture and the mixture was stirred at room temperature for 15 minutes and was vaccum filtered. The recovered product was washed 3 times with water and dried under reduced pressure to obtain 97.2 g of raw product. The latter was taken up in 120 ml of acetone and the mixture was stirred at room temperature for one hour and in an ice water bath for 30 minutes and was vacuum filtered. The recovered product was rinsed twice with a 2-1 acetone-ether mixture, then with ether and was dried under reduced pressure at 40° C. to obtain 48.72 g of purified syn isomer of 3-acetoxymethyl-7-[2-(2-tritylamino-4-thiazolyl)-2-methoxyimino-acetamido]-ceph-3-eme-4-carboxylic acid.

EXAMPLE 2

Syn isomer of 3-[(2-methyl-1,3,4-thiadiazol-5-yl)-thiomethyl]-7-[2-(2-tritylamino-4-thiazolyl)-2-methoxyimino-acetamido]-ceph-3-eme-4-carboxylic acid A mixture of 3.44 g of 3-[(2-methyl-1,3,4-thiadiazol-5-yl)-thiomethyl]-7-amino-cephalosporanic acid, 10 ml of distilled water and 22 ml of a molar sodium bicarbonate solution was stirred at room temperature for one hour during which insoluble persisted and 15 ml of acetone were added thereto. The mixture was cooled to 5° C. in an ice-methanol bath and a solution of Step A of Example 1 was added thereto over 15 minutes in a volume 10 times less. The mixture was allowed to spontaneously heat up for 90 minutes and was vacuum filtered. The filter was rinsed with water and then with acetone and 2 ml of acetic acid were added to the filtrate. The filtrate was vacuum filtered again and the filtrate was rinsed with acetone. The acetone was distilled from the filtrate in a water bath at 30° C. under reduced pressure which caused a precipitation and then 10 ml of water followed by 1.3 ml of formic acid were added thereto. The mixture was stirred at room temperature for 15 minutes and was vacuum filtered. The product was rinsed 3 times with water and was dried overnight under reduced pressure to obtain 7.895 g of raw syn isomer of 3-[(2-methyl-1,3,4-thiadiazol-5-yl)-thiomethyl]-7-[2-(2-tritylamino-4-thiazolyl)-2-methoxyimino-acetamido]-ceph-3-eme-4-carboxylic acid.

EXAMPLE 3

Syn isomer of 3-azidomethyl-7-[2-(2-tritylamino-4-thiazolyl)-2-(1-methyl-1-methoxyethoxyimino) -acetamido]-ceph-3-eme-4-carboxylic acid STEP A: Triethylamine salt of syn isomer of 2-(2-tritylamino-4-thiazolyl-2-[2-methyl-1-methoxyethoxyimino]-acetic acid A mixture of 5.01 g of the syn isomer of 2-(2-tritylamino-4-thiazolyl-2-(1-methyl-1-methoxyethoxyimino]-acetic acid [described in Belgium patent No. 865,298], 20 ml of methylene chloride and 1.5 ml of triethylamine was formed and the solvent was distilled under reduced pressure in a water bath at 30°–35° C. The residue was taken up in ether and after effloresence, the mixture was vacuum filtered. The product was rinsed with ether and dried at 40° C. under reduced pressure to obtain 5.62 g of triethylamine salt of syn isomer of 2-(2-tritylamino-4-thiazolyl-2-[1-methyl-1-methoxy-ethoxyimino]-acetic acid.

STEP B: Syn isomer of p-toluene sulfonic acid 2-(2-tritylamino-4-thiazolyl)-2-(1-methyl-1-methoxy-ethoxyimino)-acetic acid anhydride A mixture of 6.36 g of the salt of Step A, 60 ml of acetone and 2.19 g of p-toluene sulfonyl chloride was stirred at room temperature for one hour and in an ice bath for 15 minutes. The mixture was vacuum filtered and the recovered product was rinsed with acetone and dried to obtain 1.16 g of triethylamine hydrochloride. The filtrate containing syn isomer of p-toluene sulfonic acid 2-(2-tritylamino-4-thiazolyl)-2-(1-methyl-1-methoxy-ethoxyimino)-acetic acid anhydride was stored in an ice bath for the next step.

STEP C: Syn isomer of 3-azidomethyl-7-[2-(2-tritylamino-4-thiazolyl)-2-(1-methyl-1-methoxyethoxyimino)-acetamido]-ceph-3-eme-4-carboxylic acid A mixture of 2.55 g of the product of Step B, 10 ml of distilled water, 22.5 ml of a molar sodium bicarbonate solution and 10 ml of acetone was stirred at room temperature for 10 minutes and then was cooled to 5° C. in an ice-methanol bath. The solution from Step B was added over 10 minutes at 5° C. and the mixture was stirred for 2 hours while permitting spontaneous heating. The acetone was distilled from the mixture in a water bath at 30° C. under reduced pressure and the mixture was acidified by addition of 1 ml of formic acid. The mixture was vacuum filtered and the product was rinsed twice with water and taken up in ethyl acetate. The mixture was stirred at room temperature for 15 minutes and was vaccum filtered to obtain 0.36 g of the starting acid. The filtrate was dried and evaporated to dryness to obtain syn isomer of 3-azidomethyl-7-[2-(2-tritylamino-4-thiazolyl)-2-(1-methyl-1-methoxyethoxyimino)-acetamido]-ceph-3-eme-4-carboxylic acid in the form of a resin with an Rf=0.5 (70-20-10 ethyl acetate-ethanol-water mixture).

EXAMPLE 4

Syn isomer of 3-azidomethyl-7-[2-(2-tritylamino-4-thiazolyl)-2-(1-methyl-1-methoxyethoxyimino)-acetamido[-ceph-3-eme-4-carboxylic acid STEP A: Syn isomer of p-toluene sulfonyl 2-(2-tritylamino-4-thiazolyl)-2-(1-methyl-1-methoxyethoxyimino)-acetic acid anhydride A few seed crystals of triethylamine salt of the syn isomer of 2-(2-tritylamino-4-thiazolyl)-2-(1-methyl-1-methoxyethoxyimino)-acetic acid crystallized from a 1-1 acetone-ether mixture beginning from the product of Step A of Example 3 were added to a mixture of 6.03 g of the said salt, 2.28 g of p-toluene sulfonyl chloride and 30 ml of anhydrous acetone and the mixture was stirred at 20° C. for 90 minutes to obtain a thick mass. 30 ml of ether were added to the mass at 20° C. and the mixture was stirred at 20° C. for 5 minutes to homogenize the mixture which was then vacuum filtered. The product was rinsed 3 times with 10 ml of ether and was dried at 20° C. under reduced pressure to obtain 6.54 g 9f syn isomer of p-toluene sulfonyl 2-(2-tritylamino-4-thiazolyl)-2-(1-methyl-1-methoxyethoxyimino)-acetic acid anhydride and triethylamine hydrochloride. The mother liquors were evaporated to dryness and the residue was taken up in 5 ml of ether to obtain a second yield of 1 g.

To obtain the said anhydride free of triethylamine hydrochloride, the 2 drops of 7.54 g of product were dissolved in 60 ml of methylene chloride and the solution was washed twice with 30 ml of distilled water, was dried and vacuum filtered. The product was rinsed and was dried under reduced pressure at less than 30° C. to obtain 6.5 g of resin. The latter was taken up in 20 ml of ether and the mixture was stirred at 20° C. until total dissolution followed by crystallization occured. The mixture was vaccum filtered at 20° C. and the product was washed 3 times with 10 ml of ether and was dried at 20° C. under reduced pressure to obtain 5.5 g of syn isomer of p-toluene sulfonyl 2-(2-tritylamino-4-thiazolyl)-2-(-methyl-1-methoxyethoxyimino)-acetic acid anhydride.

| U.V. Spectrum (ethanol): | | |
|---|---|---|
| Inflex. towards 222 nm | $E_1^1 = 565$ | $\epsilon = 36,900$ |
| Inflex. towards 227 nm | $E_1^1 = 505$ | |
| Inflex. towards 234 nm | $E_1^1 = 403$ | $\epsilon = 26,400$ |
| Inflex. towards 260 nm | $E_1^1 = 183$ | $\epsilon = 1,200$ |
| Inflex. towards 265 nm | $E_1^1 = 163$ | |
| Inflex. towards 271 nm | $E_1^1 = 141$ | |
| Inflex. towards 300 nm | $E_1^1 = 69$ | $\epsilon = 4,500$ |
| U.V. Spectrum (0.1 HCl in ethanol): | | |
| Inflex. towards 223 nm | $E_1^1 = 564$ | |
| Inflex. towards 228 nm | $E_1^1 = 454$ | |
| Inflex. towards 264 nm | $E_1^1 = 180$ | |
| Inflex. towards 269 nm | $E_1^1 = 193$ | |
| Max. at 274 nm | $E_1^1 = 195$ | $\epsilon = 12,800$ |
| Inflex. towards 286 nm | $E_1^1 = 176$ | |

NMR Spectrum (CDCl$_3$): peaks at 1.45 ppm

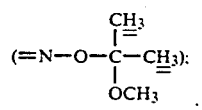

at 3.2 ppm

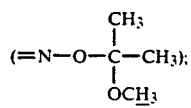

at 6.55 ppm (5-proton of thiazolyl); at 7.28 ppm (trityl proton).

STEP B: Syn isomer of 3-azidomethyl-7-[2-(2-tritylamino-4-thiazolyl)-2-(1-methyl-1-methoxy-ethoxyimino)-acetamido]-ceph-3-eme-4-carboxylic acid 0.656 g of the mixed anhydride of Step A was added in fractions over 8 minutes at −10° C. to a solution of 0.255 g of 3-azidomethyl-7-amino-ceph-3-eme-4-carboxylic acid, 2.6 ml of methylene chloride an 0.28 ml of triethylamine and after 30 minutes at −10° C., thin layer chromatography showed the disappearance of the said 3-azidomethyl acid. Two drops of acetic acid were added thereto and the mixture was washed with water, with aqueous hydrochloric acid, dried and evaporated to dryness. The residue was triturated with isopropyl ether and the mixture was vacuum filtered. The product was dried to obtain 0.691 g of syn isomer of 3-azidomethyl-7-[2-(2-tritylamino-4-thiazolyl)-2-(1-methyl-1-methoxyethoxyimino)-acetamido]-ceph-3-eme-4-carboxylic acid identical to the product of Example 3.

EXAMPLE 5

Syn isomer of 3-acetoxymethyl-7-[2-(2-tritylamino-4-thiazolyl)-2-methoxyimino-acetamido]-ceph-3-eme-4-carboxylic acid 576.5 g of the syn isomer of 2-(2-tritylamino-4-thiazolyl)-2-methoxyimino-acetic acid were added at 0° C. to a solution of 247.8 g of tosyl chloride in 780 m. of dimethylformamide and then 196 ml of triethylamine were added thereto. The mixture was held at 0° C. while adding thereto a solution of 272 g of 7-amino-cephalosporanic acid in 3 liters of ethylene chloride and 450.7 ml of triethylamine cooled to −70° to −75° C. and the mixture was held at −20° C. for 30 minutes. Then 270 ml of acetic acid followed by 540 ml of demineralized water were added thereto and the temperature rose to −15° to −20° C. 11 liters of demineralized water were added thereto and the pH was adjusted to 1 to 1.2 by addition of 0.1N hydrochloric acid. The decanted organic phase was washed 3 times with 2700 ml of demineralized water and was concentrated under reduced pressure in a bath at 8° to 30° C. to a volume of 1350 ml to obtain a solution of syn isomer of 3-acetoxymethyl-7-[2-(2-tritylamino-4-thiazolyl)-2-methoxyimino-acetamido]-ceph-3-eme-4-carboxylic acid.

The above procedure was repeated eleven times with the dimethylformamide being replaced with an equal amount of ethyl acetate, acetone, tetrahydrofuran, acetonitrile, carbon tetrachloride, methylene chloride, toluene, dioxane, isopropyl ether, N-methyl-pyrrolidone or dimethyl acetamide with similar results.

EXAMPLE 6

Syn isomer of 3-acetoxymethyl-7-[2-(2-amino-4-thiazolyl)-2-methoxyimino-acetamido]-ceph-3-eme-4-carboxylic acid 227.5 g of tosyl chloride were added with stirring over 2 to 3 minutes under an inert atmosphere to 750 ml of dimethylacetamide at 20° C. and the mixture was cooled to 0° to 2° C. with stirring under nitrogen after which 595 g of the syn isomer of 2-(2-tritylamino-4-thiazolyl)-2-methoxyimino-acetic acid were added thereto over 10 to 15 minutes at 0° to 2° C. After stirring the mixture under nitrogen at 0° to 2° C. for 15 minutes, total dissolution occured and 166 g of triethylamine were added thereto over 20 to 25 minutes at 0° to 2° C. 2.5 liters of methylene chloride were cooled to −15° to −18° C. by injection of liquid nitrogen and gaseous nitrogen and 250 g of 7-amino-cephalosporanic acid were added thereto over 3 to 4 minutes. 383 ml of triethylamine were added thereto while keeping the temperature at −15° C. and after total dissolution occured, the solution was cooled to −70° to −75° C. by injection of liquid nitrogen. The final dimethylacetamido was introduced thereto and the flask and the introduction system were rinsed twice with 50 ml of methylene chloride and the mixture was stirred at −70° to −75° C. for 30 minutes after which a solution of 250 ml of acetic acid and 125 ml of methylene chloride was added thereto at −70° to −75° C. The mixture was stirred at −70° to −75° C. and then the temperature rose to −60° C. and 500 ml of demineralized water at 0° to 5° C. were added thereto. The mixture was stirred under nitrogen while the temperature rose to −12° to −15° C. and was then poured with stirring into 10 liters of demineralized water at 18° to 20° C.

The resulting emulsion was stirred into a solution of 375 ml of 22° Bè hydrochloric acid and 375 ml of water and the decanted aqueous phase was extracted with 250 ml of methylene-chloride. The organic phase was washed 3 times with 2500 ml of demineralized water and was then concentrated under reduced pressure in a less than 30° C. to a volume of 1250 ml to obtain a syrupy solution of the syn isomer of 3-acetoxymethyl-7-[2-(2-tritylamino-4-thiazolyl)-2-methoxyimino-acetamido]-ceph-3-eme-4-carboxylic acid.

A solution of 300 ml of demineralized water and 1200 ml of 98% furnic acid was added at 18° to 20° C. to the syrupy solution and the mixture was stirred under reduced pressure at 30°–35° C. for 2½ hours. Triphenylcarbinol precipitated and the mixture was cooled to 18°–20° C. and was vaccum filtered. The product was empasted with a mixture of 625 ml of demineralized water and 312 ml of formic acid for a yield of 292.5 g of triphenylcarbinol and the formic acid was poured in one minute into 10 liters of demineralized water at 18°–20° C. The mixture was stirred at 15°–20° C. while 2500 g of ammonium sulfate were added thereto and the mixture was stirred for 15 minutes. After the addition of 1250 g of ammonium sulfate, the mixture was stirred for one hour at 15°–20° C. and was vacuum filtered. The product was empasted 3 times with 625 ml of demineralized water containing 5% formic acid at 0° to 5° C. and was dried at 20°–25° C. under reduced pressure ato obtain the formate of syn isomer of 3-acetoxymethyl-7-[2-(2-amino-4-thiazolyl)-2-methoxyimino-acetamido]-ceph-3-eme-4-carboxylic acid.

The latter product was showered into 2080 ml of pure ethanol and the mixture was heated at 50°–55° C. for 30 minutes and was cooled to 18°–20° C. The mixture was stirred for one hour and was vacuum filtered. The product was washed twice with 415 ml of pure ethanol to obtain syn isomer of 3-acetoxymethyl-7-[2-(2-amino-4-thiazolyl)-2-methoxyimino-acetamido]-ceph-3-eme-4-carboxylic acid.

EXAMPLE 7

Syn isomer of 3-acetoxymethyl-7-[2-(2-amino-4-thiazolyl)-2-methoxyimino-acetamido]-ceph-3-eme-4-carboxylic acid The process of Example 6 was repeated a number of times with the following differences to obtain syn isomer of 3-acetoxymethyl-7-[2-(2-amino-4-thiazolyl)-2-methoxyimino-acetamido]-ceph-3-eme-4-carboxylic acid:

A—The extemporaneously prepared solution of 7-amino-cephalosporanic acid was added at −40° C. rather than −70° C.

B—The 7-amino-cephalosporanic acid solution was prepared with 5 liters of methylene chloride and was cooled to −40° C.

C—7-amino-cephalosporanic acid solution was prepared with 250 ml of triethylamine and was cooled to −40° C.

D—The 7-amino-cephalosporanic acid solution was prepared with 3.7 liters of methylene chloride and 250 ml of triethylamine and was cooled to −40° C.

E—The 7-amino-cephalosporanic acid solution was prepared with 5 liters of methylene chloride and 250 ml of triethylamine and was cooled to −40° C.

F—The extemporaneously prepared 7-amino-cephalosporanic acid solution was cooled to −20° C.

G—The 7-amino-cephalosporanic acid solution was prepared with 5 liters of methylene chloride and was cooled to −20° C.

H—The 7-amino-cephalosporanic acid solution was prepared with 250 ml of triethylamine and was cooled to −20° C.

I—The 7-amino-cephalosporanic acid solution was prepared with 5 liters of methylene chloride and 250 ml of triethylamine and was cooled to −20° C.

EXAMPLE 8

Syn isomer of 3-acetoxymethyl-7-[2-(2-amino-4-thiazolyl)-2-methoxyimino-acetamido]-ceph-3-eme-4-carboxylic acid 192 g of the syn isomer of 2-(2-amino-4-thiazolylo)-2-methoxyimino-acetic acid were added with stirring under dry nitrogen to 600 ml of dimethylacetamide at 20°–25° C. and the mixture was stirred at 20°–25° C. while 133 ml of triethylamine were added thereto. After the addition, the mixture was held at 20°–25° C. and was then cooled to −15° to −17° C. after which an anhydrous solution of 182.5 g of tosyl chloride in 200 ml of dimethylacetamide was slowly added thereto at −15° to −17° C. to obtain a yellow suspension. The latter was stirred at −18° to −20° C. under nitrogen for one hour and an extemporaneously prepared solution of 7-amino-cephalosporanic acid at −70° to −75° C. was slowly added to the suspension at −18° to −20° C.

The said solution was prepared by adding 200 g of 7-amino-cephalosporanic acid at −15° to −18° C. to 200 ml of methylene chloride and then 307 ml of triethylamine were added thereto at −15° to −18° C. After total dissolution occured, the solution was cooled to −70° to −75° C. for the addition.

After the addition, the introduction system was rinsed with 100 ml of methylene chloride at −20° to −25° C. and the mixture was stirred under nitrogen at −70° to −75° C. while adding a solution of 200 ml of acetic acid in 100 ml of methylene chloride. The mixture was stirred at −70° to −75° C. and after the temperature rose to −50° C., 400 ml of demineralized water at 0° to 5° C. were added thereto. The mixture was heated to 0° to 5° C. and a solution of 400 ml of formic acid and 400 ml of demineralized water were added thereto. The mixture was seeded with 1 g of the syn isomer of Example 6 and the temperature was raised to 15° to 20° C. The methylene chloride was distilled under reduced pressure while adding 2200 ml of demineralized water. The mixture was stirred under reduced pressure at 18° to 20° C. for 30 minutes and normal pressure was then returned. The mixture was stirred at 0° to 5° C. and was then vacuum filtered and the product was empasted with 400 ml of water containing 5% of formic acid at 0° to 5° C. The product was dried at 20° to 25° C. to obtain the formate of syn isomer of 3-acetoxymethyl-7-[2-(2-amino-4-thiazolyl)-2-methoxyimino-acetamido]-ceph-3-eme-4-carboxylic acid.

The formate was screened and was showered into 1725 ml of 100% ethanol at 20°–25° C. and the mixture was stirred at 50°–55° C. for 30 minutes and was then cooled to 18°–20° C. The mixture was stirred for one hour and was vacuum filtered and the product was washed twice with 345 ml of 100% ethanol and was dried under reduced pressure to obtain syn isomer of 3-acetoxymethyl-7-[2-(2-amino-4-thiazolyl)-2-methoxyimino-acetamido]-ceph-3-eme-4-carboxylic acid.

EXAMPLE 9

Syn isomer of 3-acetoxymethyl-7-[2-(2-amino-4-thiazolyl)-2-methoxyimino-acetamido]-ceph-3-eme-4-carboxylic acid The process of Example 8 was repeated except that after addition of triethylamine to the syn isomer of 2-(2-amino-4-thiazolyl)-2-methoxyimino-acetic acid, the mixture was cooled at 0° C. and the tosyl chloride in dimethylacetamide was added over 15 to 20 minutes.

The reaction with 7-amino-cephalosporanic acid took place over 30 minutes.

EXAMPLE 10

The process of Example 8 was repeated a plurality of times with the following changes to obtain syn isomer of 3-acetoxymethyl-7-[2-(2-amino-4-thiazolyl)-2-methoxyimino-acetamido]-ceph-3-eme-4-carboxylic acid:

A—The 7-amino-cephalosporanic acid was previously cooled to −20° C.

B—The 7-amino-cephalosporanic acid solution was prepared with 4 liters of methylene chloride and was previously cooled to −20° C.

C—The 7-amino-cephalosporanic acid solution was prepared with 204 ml of triethylamine and was previously cooled to −20° C.

D—7-amino-cephalosporanic acid solution was prepared with 4 liters of methylene chloride and 204 ml of triethylamine and was previously cooled to −20° C.

EXAMPLE 11

Syn isomer of 3-[(2-methyl-1,3,4-thiadiazol-5-yl)-thiomethyl]-7-[2-(2-amino-4-thiazolyl)-2-methoxyimino-acetamido]-ceph-3-eme-4-carboxylic acid 41.5 g of tosyl chloride were added at room temperature with stirring to 150 ml of dimethylacetamide and the mixture was stirred at 0° to 2° C. for 10 minutes. 116.3 g of the syn isomer of 2-(2-tritylamino-4-thiazolyl)-2-methoxyiminoacetic acid were added thereto and the mixture was stirred at 0° C. under nitrogen while 30.25 ml of pure triethylamine were added. 50 ml of methylene chloride were added at 0° C. and the mixture was stirred under nitrogen at 0° C. and then at −15° C. to obtain solution A.

At the same time, 50 g of 3-[(2-methyl-1,3,4-thiadiazol-5-yl)-thiomethyl]-7-amino-cephalosporanic acid were added with stirring at 15° C. to a mixture of 350 ml of dimethylacetamide, 50 ml of demineralized water and 64.5 ml of triethylamine and the mixture was diluted with 500 ml of methylene chloride and was stirred under nitrogen and filtered to obtain solution B.

Solution B was cooled to −70° to −72° C. and solution A at −15° C. was slowly added to solution B and the resulting clear marron solution was stirred at −70° to −72° C. for 30 minutes and then a solution of 50 ml of pure acetic acid in 25 ml of methylene chloride were added thereto. 100 ml of demineralized water were added to the stirred solution at −70° to −72° C. while permitting the temperature to rise and the heterogenous mixture was heated to −15° C. and was poured with stirring into 2 liters of demineralized water. The pH was adjusted to 1 by addition of 150 ml of 22° Bè hydrochloric acid diluted in half and the decanted aqueous phase was extracted with 50 ml of methylene chloride. The combined organic phases were concentrated under reduced pressure to a volume of 250 ml to obtain a clear marron oil which was the syn isomer of 3-[(2-methyl-1,3,4-thiadiazol-5-yl)-thiomethyl]-7-[2-(2-tritylamino-4-thiazolyl)-2-methoxyimino-acetamido]-ceph-3-eme-4-carboxylic acid.

300 ml of formic acid containing 20% of water were added to the oil and the mixture was heated with stirring at 35° C. for 2½ hours during which triphenylmethanol crystallized. 2.5 g of carbon black were added to the mixture which was then vacuum filtered and the filter was washed with 75 ml and then 37 ml of formic acid containing 20% of water. The limip solution was poured into 2 liters of demineralized water and crystallization began. The mixture was stirred at 20° C. for 30 minutes and then 500 g of ammonium sulfate were added thereto. After stirring for 15 minutes, another 250 g of ammonium sulfate were added thereto and the mixture was vacuum filtered. The product was washed with distilled water and was dried over potassium hydroxide in an oven under reduced pressure at room temperature to obtain 53 g of raw syn isomer of 3-[(2-methyl-1,3,4-thiadiazol-5-yl)-thiomethyl]-7-[2-(2-amino-4-thiazolyl)-2-methoxyimino-acetamido]-ceph-3-eme-4-carboxylic acid.

EXAMPLE 12

Syn isomer of 3-[(2-methyl-1,3,4-thiadiazol-5-yl)-thiomethyl]-7[2-(2-amino-4-thiazolyl)-2-methoxyimino-acetamido]-ceph-3-eme-4-carboxylic acid 242 ml of triethylamine were added with stirring under an nitrogen atmosphere at room temperature to a suspension of 350 g of the syn isomer of 2-(2-amino-4-thiazolyl)-2-methoxyimino-acetic acid in 1600 ml of dimethylacetamide and the mixture was stirred for 30 minutes and was then cooled to −15° to 17° C. over 30 minutes. A solution of 332.2 g of tosly chloride in 400 ml of dimethylacetamide was added to the mixture at −15° to −17° C. which dissolved the triethylamine salt of the starting acid and crystallized triethylamine hydrochloride. The suspension was held at −18° to −20° C. for one hour and was suspension A.

400 g of 3-[(2-methyl-1,3,4-thiadiazol-5-yl)-thiomethyl]-7-amino-cephalosporanic acid were added under nitrogen at 15° C. to a mixture of 2.8 liters of dimethylacetamide. 400 ml of water and 516 ml of triethylamine and the mixture was stirred at 15° C. while 2 liters of methylene chloride were added thereto. The solution was stirred under nitrogen at −70° C. to −75° C. while suspension A was added thereto. The mixture was rinsed with 200 ml of methylene chloride at −20° to −25° C. and the mixture was stirred at −70° C. to −75° C. for 30 minutes. A solution of 400 ml of acetic acid and 200 ml of methylene chloride was added slowly at −70° to −75° C. and the mixture was stirred at −70° to −75° C. while allowing the temperature to slowly rise to −50° C. 800 ml of demineralized water were added to the mixture and at a temperature of 0° to 5° C., a mixture of 800 ml of formic acid and 800 ml of demineralized water were added thereto. Methylene chloride was distilled under reduced pressure while introducing 6.4 liters of demineralized water and a lettle crystallization occured. The suspension was held at 18° to 20° C. under reduced pressure for 30 minutes and normal pressure was resumed. The mixture was cooled a 0° for one hour and was vacuum filtered and the product was rinsed with distilled water and dried to obtain 578 g of syn isomer of 3-[(2-methyl-1,3,4-thiadiazol-5-yl)-thiomethyl]-7-[2-(2-amino-4-thiazolyl)-2-methoxyimino-acetamido]-ceph-3-eme-4-carboxylic acid.

EXAMPLE 13

Syn isomer of 1,1-dimethylethyl 7-[2-(2-tritylamino-4-thiazolyl)-2-(1-methyl-1-methoxyethoxyimino)-acetamido]-ceph-3-eme-4-carboxylate.

A mixture of 3.01 g of the syn isomer of triethylamine 2-(2-tritylamino-4-thiazolyl)-2-[(1-methyl-1-methoxyethoxyimino)-acetate and 15 ml of dry acetone was stirred at room temperature while 1.05 g tosyl chloride was added thereto all at once and the mixture was cooled to 17° C. and was stirred for 70 minutes. The acetone was distilled at 25° C. and the residue was taken up in 15 ml of ether with efflorescence. The mixture was vacuum filtered and the product was rinsed and dried to obtain 3.575 g of a mixed carboxylic acid-sulforic acid anhydride containing 0.685 g of triethylamine hydrochloride or 2.89 g of pure product identical to that of Step A of Example 3.

A solution of 0.512 g of 1,1-dimethylethyl 7-amino-3-hydro-ceph-3-eme-4-carboxylate in 5 ml of anhydrous methylene chloride was cooled in a bath at −6° C. and 0.3 ml of triethylamine and then 1.81 g of the above anhydride were added thereto. The mixture was allowed to spontaneously heat to 5° C. over 40 minutes and 2 drops of acetic acid and 5 ml of water were added thereto. The mixture was decanted and the decanted aqueous phase was extracted with methylene chloride. The organic phase was dried and vacuum filtered and the filtrate was evaporated to dryness. The residue was taken up in 6 ml of methanol and crystallization was induced. The mixture was vacuum filtered and the product was rinsed and dried to obtain 1.377 g of syn isomer of 1,1-dimethylethyl 7-[2-(2-tritylamino-4-thiazolyl)-2-(1-methyl-1-methoxyethoxyimino)-acetamido]-ceph-3-eme-4-carboxylate.

EXAMPLE 14

Syn isomer of 7-[2-(2-amino-4-thiazolyl)-2-hydroxyimino-acetamido]-ceph-3-eme-4-carboxylate acid A solution of 1.2 g of the product of Example 13 in 6 ml of trifluoroacetic acid was stirred for 25 minutes and was diluted with 60 ml of isopropyl ether. The mixture was vacuum filtered and the product was rinsed and dried to obtain 0.706 of the trifluoroacetate of syn isomer of 7-[2-(2-amino-4-thiazolyl)-2-hydroxyimino-acetamido]-ceph-3-eme-4-carboxylic acid. The said product was dissolved in 3.5 ml of aqueous sodium bicarbonate solution, and the mixture was vacuum filtered. The filter was rinsed with a minimum of water and 0.8 ml of 2N hydrochloric acid was added to the filtrate. The insolubles while crystallized were scraped and the mixture was vacuum filtered. The product was rinsed with a minimum of water and was dried to obtain 0.273 g of syn isomer of 7-[2-(2-amino-4-thiazolyl)-2-hydroxyimino-acetamido]-ceph-3-eme-4-carboxylic acid.

EXAMPLE 15

Syn isomer of 3-acetoxymethyl-7-[2-(2-amino-4-thiazolyl)-2-methoxyimino-acetamido]-ceph-3-eme-4-carboxylic acid A suspension of 77.55 g of the syn isomer of 2-(2-amino-4-thiazolyl)-2-methoxyimino-acetic acid in 243 ml of dimethylacetamide was stirred under nitrogen at 20° to 25° C. for 15 minutes and 53.7 ml of triethylamine were added thereto over 30 minutes at 20°-25° C. The mixture was stirred at 20°-25° C. for 30 minutes and then cooled to −15° to −17° C. A solution of 30 ml of methane sulfonyl chloride in 81.2 ml of dimethylacetamide was added over one hour to the mixture at −15° to −17° C. and the resulting suspension (A) was held at −18° to −20° C. for 2 hours.

115 ml of triethylamine were added at −15° to −17° C. over 10 minutes to a solution of 75 g of 7-aminocephalosporanic acid in 750 ml of methylene chloride and after total dissolution occurred, the solution (B) was cooled to −70° to −75° C. Solution A at −18° to −20° C. was added to solution B over 90 minutes and the mixture was rinsed with 37.5 ml of methylene chloride at −20° to −25° C. and stirred at −70° to −75° C. for 30 minutes. A solution of 75 ml of acetic acid and 75 ml of methylene chloride was added over 10 to 15 minutes at −70° to −75° C. to the mixture which was then stirred at −70° to −75° C. for 5 minutes. 150 ml of demineralized water were added to the mixture over 5 to 10 minutes after the temperature rose to −50° C. and when the temperature rose to −30° to −25° C., the mixture was filtered while keeping the filtrate at 0° to 2° C. 150 ml of formic acid and 150 of demineralized water were added to the filtrate followed by the addition of 400 ml of the formate of the syn isomer of 3-acetoxymethyl-7-[2-(2-amino-4-thiazolyl)-2-methoxyiminoacetamido]-ceph-3-eme-4-carboxylic acid as a seed agent. The mixture was moderately stirred for 90 minutes and then 825 ml of iced demineralized water were added thereto. The mixture was stirred at 0° to 2° C. for 2 hours and was vacuum filtered. The crystalline product was washed with water and dried under reduced pressure to obtain 125 g of the formate of the syn isomer of 3-acetoxymethyl-7-[2-(2-amino-4-thiazolyl)-2-methoxyimino-acetamido]-ceph-3-eme-4-carboxylic acid. 100 g of the product and 480 ml of absolute ethanol were stirred for 3½ hours at 20° to 25° C. and the mixture was vacuum filtered. The product was washed twice with 50 ml of ethanol and dried under reduced pressure to obtain 90 g of the desired syn isomer (88.7% yield).

EXAMPLE 16

Syn isomer of 3-acetoxymethyl-7-[2-(2-amino-4-thiazolyl)-2-methoxyimino-acetamido]-ceph-3-eme-4-carboxylic acid 77.6 g of the syn isomer of 2-(2-amino-4-thiazolyl)-2-methoxyimino-acetic acid were added under nitrogen at 20° C. to 225 ml of dimethylacetamide and the mixture was stirred at 20° C. for 15 minutes after which 39 g of pure triethylamine were added thereto. The mixture was stirred at 20° C. for one hour and was then cooled to −18° C. after which 68.1 g of benzene sulfonyl chloride were added thereto. The mixture was stirred at −18° C. for one hour to obtain suspension A. A solution B was prepared as in Example 15 and the procedure of Example 15 was followed to obtain after purification 86.75 g (85.5% yield) of the syn isomer of 3-acetoxymethyl-7-[2-(2-amino-4-thiazolyl)-2-methoxyimino-acetamido]-ceph-3-eme-4-carboxylic acid.

EXAMPLE 17

Syn isomer of 3-methyl-7-[2-(2-amino-4-thiazolyl)-2-methoxyimino-acetamido]-ceph-3-eme-4-carboxylic acid 71 g of the syn isomer of 2-(2-amino-4-thiazolyl)-2-methoxyimino-acetic acid were added under nitrogen at 20° to 25° C. to 280 ml of dimethylacetamide and the mixture was stirred for 15 minutes after which 42.3 ml of triethylamine were added at 20° to 25° C. over 30 minutes. The mixture was stirred for 30 minutes and cooled to −15° to −17° C. A solution of 58 g of tosyl chloride in 70 ml of dimethylacetamide were added at −15° to −17° C. over one hour to the mixture and held at −15° to −17° C. for one hour to obtain suspension A.

75 ml of demineralized water were added over 15 to 18 minutes under nitrogen at 20° C. to a solution of 50 g of 7-amino-desacetoxy-cephalosporin in 350 ml of dimethylacetamide followed by the addition of 68 ml of triethylamine over 15 minutes. The mixture was stirred at 18° to 20° C. for 15 minutes and then 200 ml of methylene chloride were added thereto to obtain solution B. The mixture was stirred at −70° to −72° C. while adding suspension A thereto over one hour. The mixture was rinsed twice with 25 ml of methylene chloride and was stirred under nitrogen at −70° to −72° C. for one hour. A mixture of 80 ml of 22° Bé hydrochloric acid and 100 ml of demineralized water were added to the mixture over 15 to 20 minutes while the temperature rose to −50° C. and the mixture was heated to 18° to 20° C. under nitrogen with stirring. the methylene chloride was distilled under reduced pressure and the remainder was added to 2 liters of demineralized water. 200 g of sodium chloride were added to the mixture which was stirred for 2 hours at 18° to 20° C. and was vacuum filtered. The recovered product was washed six times with 100 ml of water and dried under reduced pressure to obtain 82 g of the syn isomer of 3-methyl-7-[2-(2-amino-4-thiazolyl)-2-methoxyimino-acetamido]-ceph-3-eme-4-carboxylic acid hydrochloride.

The said hydrochloride was suspended at 20° C. in 820 ml of 90% ethanol and the suspension was refluxed while 1 ml of 22° Bé was added thereto. The mixture was filtered hot and the filter was rinsed with 41 ml of 90% ethanol. 25 ml of triethylamine were added with stirring over 15 minutes to the filtrate at 45° to 50° C. and the mixture was then stirred at 18° to 20° C. for 2 hours and was vacuum filtered. The product was washed 3 times with 83 ml of ethanol and 3 times with 82 ml of demineralized water and dried at 40° C. under reduced pressure to obtain 66 g (64.6 g on dry basis) of the syn isomer of 3-methyl-7-[2-(2-amino-4-thiazolyl)-2-methoxyimino-acetamido]-ceph-3-eme-4-carboxylic acid. A second yield of 4.7 g of the product was obtained under the same conditions for a total yield of 69.3 g (75.1% yield).

COMPARATIVE EXAMPLE 18

227.5 g of tosyl chloride were added with stirring over 2 to 3 minutes under an inert atmosphere to 750 ml of dimethylacetamide at 20° C. and the mixture was cooled to 0° to 2° C. with stirring under nitrogen after which 595 g of the syn isomer of 2-(2-tritylamino-4-thiazolyl)-2-methoxyimino-acetic acid were added thereto over 10 to 15 minutes at 0° to 2° C. After stirring the mixture under nitrogen at 0° to 2° C. for 15 minutes, total dissolution occurred and 166 g of triethylamine were added thereto over 20 to 25 minutes at 0° to 2° C.

2.5 liters of methylene chloride were cooled to −15° to −18° C. by injection of liquid nitrogen and gaseous nitrogen and 250 g of 7-amino-cephalosporanic acid (7 ACA) purity=92.6%) were added thereto over 3 to 4 minutes. 383 ml of triethylamine were added thereto while keeping the temperature at −15° C and after total dissolution occured, the solution was cooled −70° to −75° C. by injection of liquid nitrogen. The final dimethylacetamide was introduced thereto and the flask and the introduction system were rinsed twice with 50 ml of methylene chloride and the mixture was stirred at −70° to −75° C. for 30 minutes after which a solution of 250 ml of acetic acid and 125 ml of methylene chloride was added thereto at −70° to −75° C. The mixture was stirred at −70° to −75° C. and then the temperature rose to −60° C. and 500 ml of demineralized water at 0° to 5° C. were added thereto. The mixture was stirred under nitrogen while stirring into 10 liters of demineralized water at 18° to 20° C.

The resulting emulsion was stirred into a solution of 375 ml of 22° Bé hydrochloric acid and 375 ml of water and the decanted aqueous phase was extracted with 250 ml of methylene chloride. The organic phase was washed 3 times with 2500 ml of demineralized water and was then concentrated under reduced pressure at less than 30° C. to a volume of 1250 ml to obtain a syrupy solution of the syn isomer of 3-acetoxymethyl-7-[2-(2-tritylamino-4-thiazolyl)-2-methoxyimino-acetamido]-ceph-3-eme-4-carboxylic acid.

A solution of 300 ml of demineralized water and 1200 ml of 98% formic acid were added at 18° to 20° C. to the syrupy solution and the mixture was stirred under reduced pressure at 30°-35° C. for 2½ hours. Triphenylcarbinol precipitated and the mixture was cooled to 18°-20° C. and was vacuum filtered. The product was empasted with a mixture of 625 ml of demineralized water and 312 ml of formic acid for a yield of 292.5 g of triphenylcarbinol and the formic acid was poured in one minute into 10 liters of demineralized water at 18°-20° C. The mixture was stirred at 15°-20° C. while 2500 g of ammonium sulfate were added thereto and the mixture was stirred for 15 minutes. After the addition of 1250 g of ammonium sulfate, the mixture was stirred for one hour at 15°-20° C. and was vacuum filtered. The product was empasted 3 times with 625 ml of demineralized water containing 5% formic acid at 0° to 5° C. and was dried at 20°-25° C. under reduced pressure to obtain the formate of syn isomer of 3-acetoxymethyl-7-[2-(2-amino-4-thiazolyl)-2-methoxyimino-acetamido]-ceph-3-eme-4-carboxylic acid.

The latter product was showered into 2,080 ml of pure ethanol and the mixture was heated at 50°-55° C. for 30 minutes and was cooled to 18°-20° C. The mixture was stirred for one hour and was vacuum filtered. The product was washed twice with 415 ml of pure ethanol to obtain syn isomer of 3-acetoxy-methyl-7-[2-(2-amino-4-thiazolyl)-2-methoxyimino-acetamido]-ceph-3-eme-4-carboxylic acid.

That in this example 375 g of raw product was obtained (corresponding to 340.8 g of dry product: yield=88% respect to 7 ACA).

After purification 327 g of purified product were obtained (corresponding to 294 g of dry product: final yield=76%).

That the same product was previously obtained from the same starting materials (syn isomer of 2-(2-tritylamino-4-thiazolyl)-2-methoxyimino-acetic acid and 7 ACA) by using symetrical carboxylic anhydrides. Such a process is described e.g. in U.S. Pat. No. 4,152,432 Example 3 Step D an Example 4 (removal of the trityl group).

The process using symetrical carboxylic anhydride is as follows:

Example 3, Step D of U.S. Pat. No. 4,152,432

3-acetoxymethyl-7-[2-(2-tritylamino-4-thiazolyl)-2-methoxyiminoacetamido]-ceph-3-eme-4-carboxylic acid 0.78 g of dicyclohexylcarbodiimide was added to a solution of 2.9 g of 2-(2-tritylamino-4-thiazolyl)-2-methoxyimino-acetic acid syn isomer in 30 ml of dry methylene chloride and the mixture was stirred for an hour at room temperature and was then vacuum filtered to remove dicyclohexyl urea formed. The filtrate was cooled to $-10°$ C. and a solution of 1.01 g of pure 7-amino-cephalosporanic acid in 13 ml of methylene chloride and 0.9 ml of triethylamine was added. The temperature returned to room temperature and 1 ml of acetic acid was added thereto. The mixture was vacuum filtered and the filtrate was washed with aqueous hydrochloric acid, dried and concentrate to dryness. The residue was taken up in 10 ml of dioxane and 1 ml of water and 3 ml of a saturated sodium bicarbonate aqueous solution were added thereto. The mixture was stirred and vacuum filtered and the filtrate was washed and evaporated to dryness. The residue was taken up in methylene chloride and the solution was washed with 10 ml of water and 5 ml of N hydrochloric acid. The mixture was decanted and the organic phase was washed with water, dried and effloresced with ether to obtain 1.747 g of raw product. The latter was dissolved in ethyl acetate and was crystallized by addition of ether to obtain 1.255 g of pure 3-acetoxymethyl-7-[2-(2-tritylamino-4-thiazolyl)-2-methoxyiminoacetamido]-ceph-3-eme-4-carboxylic acid in the syn configuration. Yield 48.4%.

Example 4, of U.S. Pat. No. 4,152,432

3-acetoxymethyl-7-[2-(2-amino-4-thiazolyl)-2-methoxyiminoacetamido]ceph-3-eme-4-carboxylic acid A mixture of 0.975 g of the product of Example 3 in 4 ml of 50% aqueous formic acid was stirred at 55° C. for 10 minutes and 4 ml of water were added thereto. The mixture was vacuum filtered and the filtrate was evaporated to dryness under reduced pressure. The residue was effloresced with 2 ml of ethanol and was vacuum filtered. The product was washed with ethanol and then with ether to obtain 0.428 g of pure 3-acetoxymethyl-7-[2-(2-amino-4-thiazolyl)-2-methoxyiminoacetamido]-ceph-3-eme-4-carboxylic acid with a syn configuration. Yield = 67.25%.

The final yield is therefore 32.5% with respect to 7~ACA.

Conclusion

The use of the sulfonic-carboxylic anhydrides instead of the symetrical carboxylic anhydrides results in a dramatic and unexpected increase in the yield of the final product.

Various modifications of the products and processes of the invention may be made without departing from the spirit or scope thereof and it is to be understood that the invention is intended to be limited only as defined in the appended claims.

What we claim is:

1. A process for the preparation of syn isomers of cephalosporanic acid compounds of the formula

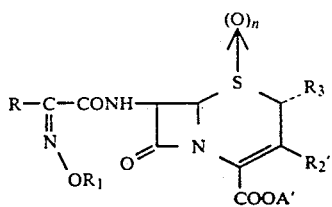

wherein R is selected from the group consisting of thiazolyl, aminothiazolyl and protected aminothiazolyl optionally substituted with a halogen, $R_1$ is selected from the group consisting of hydrogen, protective groups of the hydroxy selected from the group consisting of ethoxycarbonyl, methoxycarbonyl, propoxycarbonyl, benzyloxycarbonyl, tert.-butoxycarbonyl, 1-cyclopropylethoxycarbonyl, tetrahydropyanyl, tetrahydrothiopyranyl, methoxytetrahydropyranyl, trityl, benzyl, 4-methoxybenzyl, benzyhydryl, trichloroethyl, 1-methyl-1-methoxyethyl and phthaloyl, alkyl of 1 to 6 carbon atoms, alkenyl and alkynyl of 2 to 6 carbon atoms and cycloalkyl of 3 to 6 carbon atoms and acyl of an organic carboxylic acid of 1 to 18 carbon atoms and $R'_2$ and $R_3$ are both hydrogen or $R'_2$ is hydrogen and $R_3$ is alkyl of 1 to 4 carbon atoms or $R_3$ is hydrogen and $R'_2$ is selected from the group consisting of halogen, alkyl of 1 to 5 carbon atoms, alkoxy of 1 to 5 carbon atoms, alkylthio of 1 to 5 carbon atoms, cycloalkyl of 3 to 5 carbon atoms, acetoxymethyl, carbamoyloxymethyl,

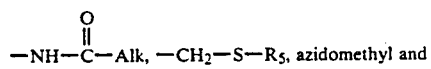

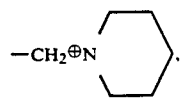

Alk is alkyl of 1 to 4 carbon atoms, $R_5$ is selected from the group consisting of 1-methyltetrazolyl, 2-methyl-1,3,4-thiadiazolyl, 3-methyl-1,2,4-thiadiazol-5-yl, 3-methoxy-1,2,4-thiadiazolyl, 1,3,4-thiadiazol-5-yl, 2-amino-1,3,4-thiadiazol-5-yl, 3-hydroxycarbonyl-methyl-1,2,4-thiadiazol-5-yl, 5-methoxy-1,2,4-thiadiazol-3-yl, 4-methyl-5-hydroxycarbonyl-methyl-1,3-thiazol-2-yl, 1-dimethyl-aminoethyl-1,2,3,4-tetrazol-5-yl, 1,3,4-triazol-5-yl, 2-(thien-2-yl)-1H-1,3,4-triazol-5-yl, 1-amino-2-trifluoromethyl-1,3,4-triazol-5-yl, 4-hydroxycarbonylmethyl-1,3-thiazol-2-yl and acyl of an alkanoic acid of 2 to 4 carbon atoms, A' is selected from the group consisting of hydrogen, alkali metal cations, alkaline earth metal cations, magnesium cation, ammonium ion, a non-toxic, pharmaceutically acceptable organic amine salt and the remainder of a non-toxic, pharmaceutically acceptable alcohol or COOA' is COO$^-$ when $R'_2$ is pyridinium methyl, n is an integer from 0 to 2 comprising reacting first in a solvent and optionally in the presence of a base, a compound of the formula

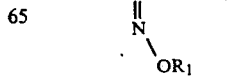

wherein R and $R_1$ have the above definition and $A_1$ is selected from the group consisting of hydrogen, alkali metal cation, alkaline earth metal cations, magnesium cation, —$NH_4$ cation and an organic amine base, with a compound of the formula

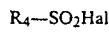

$$R_4\text{—}SO_2Hal \quad\quad\quad III$$

wherein $R_4$ is selected from the group consisting of optionally substituted alkyl, aryl and aralkyl and Hal is a halogen and reacting the resulting product in a solvent and optionally in the presence of a base with a compound of the formula

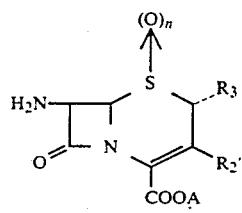

wherein $R'_{2n}$, A' and $R_3$ are defined as above to obtain the compound of formula I'.

2. The process of claim 1 wherein $R'_2$ has a value other than

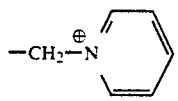

and COOA' is other than COO⁻.

3. The process of claim 2 for the preparation of the syn isomer of a compound of the formula

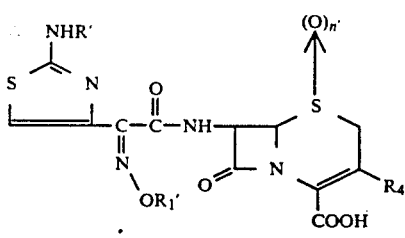

wherein R' is selected from the group consisting of hydrogen and an amino protective group, $R'_1$ is selected from the group consisting of hydroxy protective group, alkyl of 1 to 4 carbon atoms optionally substituted with a free or esterified carboxyl and alkenyl and alkynyl of 2 to 4 carbon atoms, $R_4$ is selected from the group consisting of hydrogen and —$CH_2$—$R''_2$ $R''_2$ is selected from the group consisting of acetoxy, 1-methyl-1(H)-tetrazol-5-ylthio, 2-methyl-1,3,4-thiadiazolythio and azido and n' is 0 or 1, comprising reacting in a solvent and in the optional presence of a base, a compound of the formula

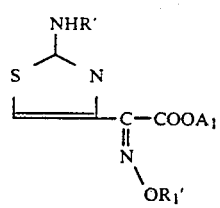

wherein R' and $R'_1$ have the above definition and $A_1$ is selected from the group consisting of hydrogen, alkali metal, alkaline earth metal, —$NH_4$, magnesium and an organic amine base with tosyl chloride and reacting the resulting product in a solvent and in the presence of a base with a compound of the formula

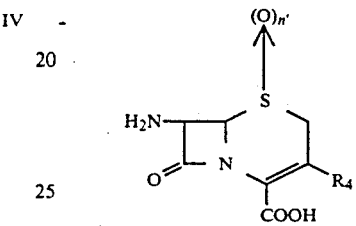

wherein n' and $R_4$ have the above definition.

4. The process of claim 3 wherein $R'_1$ is selected from the group consisting of methyl and isopropyl optionally substituted with alkoxy carbonyl of 2 to 6 carbon atoms.

5. The process of claim 1 wherein the solvent for the reaction of compounds of formulae II and III is selected from the group consisting of acetone, dimethylacetamide, ethyl acetate, tetrahydrofuran, acetonitrile, carbon tetrachloride, methylene chloride, toluene, dioxane, isopropyl ether, N-methyl-pyrrolidone and dimethylformamide.

6. The process of claim 5 wherein the solvent is dimethylacetamide.

7. The process of claim 1 wherein the solvent from the second step is selected from the group consisting of methylene chloride and aqueous dimethylacetamide.

8. The process of claim 1 wherein the optionally present base is triethylamine.

9. The process of claim 1 wherein both steps are effected at low temperatures.

10. The process of claim 1 wherein the compound of formula III is tosyl chloride.

11. The process of claim 1 comprising reacting at low temperature, in dimethylacetamide, in the presence of triethylamine, tosyl chloride and the syn isomer of 2-(2-amino-4-thiazolyl)-2-methoxyimino-acetic acid and reacting the resulting product with 7-amino-cephalosporanic acid in methylene chloride in the presence of triethylamine to obtain the syn isomer of 3-acetoxymethyl-7[2-(2-amino-4-thiazolyl)-2-methoxyimino-acetamido]-ceph-3-eme-4-carboxylic acid.

12. The process of claim 1 comprising reacting at low temperature in dimethylacetamide, in the presence of triethylamine, tosyl chloride and the syn isomer of 2-(2-tritylamino-4-thiazolyl)-2-methoxyimino-acetic acid and reacting the resulting product with 7-amino-cephalosporanic acid in methylene chloride in the presence of triethylamine to obtain the syn isomer of 3-acetoxymethyl-7-[2-tritylamino-4-thiazolyl)-2-methoxyimino-acetamido]-ceph-3-eme-4-carboxylic acid.

13. The process of claim 1 comprising reacting at low temperatures, in dimethylacetamide, in the presence of triethylamine, tosyl chloride and the syn isomer of 2-(2-amino-4-thiazolyl)-2-methoxyimino-acetic acid and reacting the resulting product with 3-[(2-methyl-1,3,4-thiadiazol-5-yl)-thiomethyl]-7-amino-cephalosporanic acid in aqueous dimethylacetamide in the presence of triethylamine to obtain the syn isomer of 3-[(2-methyl-1,3,4-thiadiazol-5-yl)-thiomethyl]-7-[2-(2-amino-4-thiazolyl)-2methoxyimino-acetamido]-ceph-3-eme-4-carboxylic acid.

14. The process of claim 1 comprising reacting at low temperatures in dimethylacetamide, in the presence of triethylamine, tosyl chloride and the syn isomer of 2-(2-tritylamino-4-thiazolyl)-2-methoxyimino-acetic acid and reacting the resulting product with 3-[(2-methyl-1,3,4-thiadiazol-5-yl)-thiomethyl]-7-amino-cephalosporanic acid in aqueous dimethylacetamide in the presence of triethylamine to obtain the syn isomer of 3-[(2-methyl-1,3,4-thiadiazol-5-yl)-thiomethyl]-7-[2-(2-tritylamino-4-thiazolyl)-2-methoxyimino-acetamido]-ceph-3-eme-4-carboxylic acid.

* * * * *